United States Patent
Swazey et al.

(10) Patent No.: US 10,292,927 B2
(45) Date of Patent: May 21, 2019

(54) MICROFIBROUS CELLULOSE COMPOSITION COMPRISING FERMENTATION MEDIA AND SURFACTANT

(71) Applicant: CP Kelco U.S., Inc., Atlanta, GA (US)

(72) Inventors: John Swazey, San Diego, CA (US); Neil Morrison, San Diego, CA (US); Zhi-fa Yang, San Diego, CA (US); Jacqueline Compton, San Diego, CA (US); Tim Nolan, Chula Vista, CA (US)

(73) Assignee: CP Kelco U.S., Inc., Atlanta, GA (US)

( * ) Notice: Subject to any disclaimer, the term of this patent is extended or adjusted under 35 U.S.C. 154(b) by 234 days.

(21) Appl. No.: 13/862,031

(22) Filed: Apr. 12, 2013

(65) Prior Publication Data
US 2014/0128480 A1    May 8, 2014

Related U.S. Application Data

(60) Provisional application No. 61/624,086, filed on Apr. 13, 2012.

(51) Int. Cl.
| | | |
|---|---|---|
| *A61K 8/73* | (2006.01) | |
| *A61Q 5/02* | (2006.01) | |
| *A61Q 5/12* | (2006.01) | |
| *A61Q 19/10* | (2006.01) | |
| *C11D 3/22* | (2006.01) | |
| *A61Q 19/00* | (2006.01) | |

(52) U.S. Cl.
CPC .............. *A61K 8/731* (2013.01); *A61Q 5/02* (2013.01); *A61Q 5/12* (2013.01); *A61Q 19/007* (2013.01); *A61Q 19/10* (2013.01); *C11D 3/222* (2013.01)

(58) Field of Classification Search
None
See application file for complete search history.

(56) References Cited

U.S. PATENT DOCUMENTS

| | | | | |
|---|---|---|---|---|
| 5,079,162 A | * | 1/1992 | Ben-Bassat | A61L 15/28 435/101 |
| 5,951,910 A | * | 9/1999 | Skaggs | C09K 3/00 106/13 |
| 6,241,812 B1 | | 6/2001 | Smith et al. | |
| 7,776,807 B2 | * | 8/2010 | Canto et al. | 510/151 |
| 7,888,308 B2 | * | 2/2011 | Swazey | 510/470 |
| 8,053,216 B2 | | 11/2011 | Yang et al. | |
| 8,772,359 B2 | * | 7/2014 | Swazey | 516/31 |
| 2004/0267006 A1 | * | 12/2004 | Yamane | C08B 15/08 536/56 |
| 2007/0027108 A1 | | 2/2007 | Yang et al. | |
| 2008/0108541 A1 | * | 5/2008 | Swazey | 510/535 |
| 2008/0108714 A1 | * | 5/2008 | Swazey et al. | 516/31 |
| 2010/0016575 A1 | * | 1/2010 | Yang et al. | 536/56 |

FOREIGN PATENT DOCUMENTS

WO    WO2011056951    *    5/2011    .............. C11D 3/22

OTHER PUBLICATIONS

Preliminary Report on Patentability and Written Opinion of the International Search Authority, PCT/US2013/026355, dated Oct. 23, 2014.
PCT/US2013/026355 International Search Report and Written Opinion dated May 12, 2013.

* cited by examiner

*Primary Examiner* — Kevin S Orwig
(74) *Attorney, Agent, or Firm* — Eversheds Sutherland (US) LLP

(57) ABSTRACT

Microfibrous cellulose (MFC) broths are provided having improved performance as compared to wet cake microfibrous cellulose (MFC) and powdered microfibrous cellulose (MFC). In embodiments, compositions having an effective amount of an MFC broth and an effective amount of a surfactant have an improved yield value as compared to a composition having a surfactant and a wet cake MFC, a powdered MFC, or a combination thereof at the same concentration as the MFC broth. Also, methods are provided for improving the yield value of surfactant compositions by adding an effective amount of a microfibrous cellulose broth to an effective amount of surfactant to provide a surfactant composition having a yield value that is higher than a composition having the surfactant and a wet cake MFC, a powdered MFC, or a combination thereof at the same concentration as the microfibrous cellulose broth.

27 Claims, No Drawings

MICROFIBROUS CELLULOSE COMPOSITION COMPRISING FERMENTATION MEDIA AND SURFACTANT

CROSS-REFERENCE TO RELATED APPLICATIONS

The present application claims priority under 35 U.S.C. § 119(e) to U.S. Provisional Application No. 61/624,086 filed Apr. 13, 2012, the disclosure of which is incorporated herein by reference in its entirety.

BACKGROUND

The present application generally relates to an improved viscosity modifier. In particular, the present application relates to microfibrous cellulose (MFC) having improved performance.

Viscosity modifiers are used in a variety of products—from foods, pharmaceuticals, and cosmetics to oil field drilling fluids. One such viscosity modifier is microfibrous cellulose (MFC), also known as reticulated cellulose or as microfibrillated cellulose, which may be produced by fermentation of *Acetobacter xylinum*. This bacteria produces cellulose that is chemically identical to plant-derived cellulose. Although identical in chemical structure, bacterial-produced MFC fibers may be smaller in diameter than plant-derived cellulose fibers, thereby giving the MFC a greater surface area. This high surface area allows MFC to create three-dimensional networks that produce a desirable yield value in solution at low use levels.

MFC is essentially insoluble and uncharged and, therefore, may be not adversely affected by ionic environments. Because MFC is essentially insoluble, it does not compete for water and, therefore, has a wide range of compatibility and is much less susceptible to degradation than water-soluble polysaccharides. For example, MFC is compatible with both concentrated anionic aqueous solutions, such as heavy brines used in oilfield applications, and in high surfactants systems, such as liquid dish and laundry detergents (see, e.g., U.S. Published Patent Application Nos. 2008/0108541 and 2008/0108714). MFC also is compatible with cationic systems, such as fabric softeners using cationic softening agents and anti-microbial cleaners that use benzylalkonium chlorides (see, e.g., U.S. Pat. No. 6,241,812 and U.S. Pat. No. 7,888,308). MFC also can be used in polyol systems (see, e.g., U.S. Pat. No. 5,951,910) such as in essentially pure glycerin, ethylene glycol, propylene glycol, and polyethylene glycol systems.

MFC has been produced commercially in several different forms. For example, CP Kelco produced a commercial MFC in the form of a wet cake (resembling wet cardboard) for several years that was later discontinued. This form of MFC was typically about 10-20 wt % solids and the balance water. A small amount of sorbic acid preservative was added to prevent mold. This form of MFC was processed using multiple rinse cycles, which led to significant product loss in recovery, and also included strong alkali treatment, which appears to have led to a decrease in MFC efficiency.

Dry powder forms of MFC also are commercially available, including both discontinued products (e.g., PrimaCel™) and presently available products (e.g., AxCel® PX, AxCel® CG-PX, Axcel® PG, Cellulon® PX, and various "K"-named products available from CP Kelco, Atlanta, Ga.). Dry powder forms were created to improve handling and logistics for delivery to customers (e.g., issues and costs associated with transporting water). These commercial versions of powdered MFC can be used to provide suspension in many applications, such as surfactant-thickened and high surfactant systems (see, e.g., U.S. Published Patent Application Nos. 2008/0108541 and 2008/0108714, and U.S. Pat. No. 7,888,308, the disclosures of which are herein incorporated by reference for their relevant teachings on MFC and MFC/surfactant systems). These commercial versions of powdered MFC generally include blends of MFC and various co-agents, such as, but not limited to, carboxymethyl cellulose (CMC), xanthan gum, guar, pectin, gellan, carrageenan, locust bean gum, gum Arabic, cationic guar, cationic hydroxyethyl cellulose (HEC), and the like. Additional information regarding MFC systems can be found, for example, in U.S. Published Patent Application No. 2007/0027108 and U.S. Pat. No. 8,053,216, the disclosures of which are incorporated herein by reference for their relevant teachings on MFC and MFC systems with co-agents.

These co-agents allow the drying and milling of MFC into a powdered product. Without these co-agents, MFC can lose a high degree of its functionality after drying and milling due to an irreversible agglomeration of the MFC during the drying process known as hornification. Blends of MFC with co-agents, however, may limit how the powdered MFC can be used in products due to compatibility limitations of the co-agents. For example, while MFC is uncharged, most of the co-agents that are used are either anionic or cationic. Thus, commercial MFC powdered products containing anionic co-agents, such as CMC or xanthan gum, may have compatibility issues when used in products with, for instance, cationic surfactants. Additionally, commercial MFC powdered products may have limited compatibility with products that contain high levels of water-miscible organic solvents, such as glycols or glycerol. When used with such organic solvents, the co-agents from the commercial MFC may form precipitates which may result in poor clarity and poor yield values (i.e., poor suspension properties). Finally, the use of activated solutions (i.e., highly dispersed solutions of MFC prepared by using high shear mixing such as high speed rotor stator devices or high pressure homogenization devices) of powdered MFC may restrict the order in which other ingredients are added to a product formulation, so as to prevent issues such as co-agents forming precipitates.

In addition, it has recently been discovered that irreversible losses in the MFC performance may result from manufacturing of the wet-cake and dry powdered forms of the MFC. For example, the wet-cake MFC was purified by lysing the bacteria cells during a highly caustic, hot-digestion step which was believed to be necessary to solubilize the cellular debris for subsequent removal during washing steps in the process. The processing of the wet-cake MFC began immediately after fermentation with a concentration step using a belt press. The concentrated MFC was then re-slurried with soft water to a concentration of around 2% by weight MFC, and the pH was raised to about 13. The MFC slurry was then held at pH 13 for about 3 hours at 150° F. Following the caustic digestion, the material was again concentrated and re-slurried in soft water up to 4 times. These treatments appear to have led to significant losses of MFC fiber and resulted in reduced performance.

Accordingly, there exists a need to provide a form of MFC product for use in a wide variety of product formulations that increases the efficiency of the MFC over current commercially available forms of MFC.

SUMMARY

Embodiments of the present description include compositions having an effective amount of an MFC broth and an effective amount of a surfactant. The compositions have an improved yield value as compared to a comparative composition having the surfactant and a wet cake MFC, a powdered MFC, or a combination thereof at the same concentration as the MFC broth.

In another aspect, methods are provided for improving the yield value of surfactant compositions, including combining an effective amount of a microfibrous cellulose broth and an effective amount of a surfactant to produce a surfactant composition having a yield value that is higher than a comparative composition having the surfactant and a wet cake MFC, a powdered MFC, or a combination thereof at the same concentration as the microfibrous cellulose broth.

DETAILED DESCRIPTION

Before the present methods are disclosed and described, it is to be understood that the aspects described below are not limited to specific embodiments, specific embodiments as such may, of course, vary. It is also to be understood that the terminology used herein is for the purpose of describing particular aspects only and is not intended to be limiting.

It must be noted that, as used in the specification and the appended claims, the singular forms "a," "an," and "the" include plural references unless the context clearly dictates otherwise. Thus, for example, reference to "a co-agent" include mixtures of two or more such co-agents or references to "a bleaching" or "an oxidizing agent" includes mixtures of two or more such agents.

Ranges may be expressed herein as from "about" one particular value and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint.

A weight percent of a component, unless specifically stated to the contrary, is based on the total weight of the formulation or composition in which the component is included.

It has been found that MFC in its broth form is particularly convenient and efficient relative to other forms of MFC. The broth can either be used "as is" directly from the fermenter or can undergo further processing steps to deodorize and sterilize the broth. "Broth," as used herein, does not refer to a wet cake or a powder form MFC. Rather, "broth", as used herein, means a fermentation media comprising a usable amount of microbially produced MFC. "Broth," as used herein, also may include a fermentation media that is further processed, so long as the character of the MFC is not significantly changed such that the MFC loses its original efficiency (e.g., as may occur after treatment of the MFC with an alkali at pH 13 and 150° F. and several dewatering steps on a belt press). For example, as used herein, the "efficiency" or "effectiveness" of the MFC may be characterized by the yield stress it imparts (e.g., the polished fermentation media may have a 20%, 30%, 40%, or higher increase in yield stress as compared to that of wet-cake MFC).

Thus, the broth form of microfibrous cellulose (MFC), whether concentrated or not, functions better in terms of providing a higher yield stress per gram of cellulose in surfactant systems than previous forms of commercially produced MFC (e.g., wet-cake form like Cellulon® or dry powders like AxCel® PX, AxCel® CG-PX, Cellulon® PX, Cellulon® LC, etc.). The enhanced performance is both surprising and unexpected because it was thought that no significant differences would be observed between the wet-cake version of MFC and a broth version. Not wishing to be bound by any theory, it is believed that the broth version of MFC may perform better than the wet-cake form of MFC in part due to the high temperature, high alkali treatment and pressing that the wet-cake form of MFC is subjected to during its processing. These treatments previously were required to provide a product that could be spray dried for food grade applications and were conventional methods of purification when wet-cake MFC was commercially available. The broth form of MFC, however, has never been commercially available because most consumers desired wet-cake or dry powder forms of MFC. Thus, the use of MFC broth in stabilizing surfactant systems has not been previously observed, recognized, or quantified.

The MFC broth may be prepared using known methods of fermenting *Acetobacter xylinum*. No special media, temperature or pressure are required. A fermentation broth of *A. xylinum* typically produces microfibrous cellulose at levels from about 0.5 to about 2.0 g/liter. The remainder of the broth is predominately water with low levels of residual sugars, proteins, cellular debris, and a trace amount of a variety of salts used to provide the bacteria its required nutrients and pH control. The use of MFC directly from the broth generally poses no significant problems because such products generally have no influence on the final industrial application. At the end of the fermentation cycle, the active microorganisms may be killed by pasteurization at a suitable temperature and/or chemical treatment.

The present application recognizes the benefits of using untreated or mildly treated MFC broth to realize the highest possible efficiency of MFC in many applications, including surfactant systems and polyol systems. Because a completely untreated broth may not be commercially desirable due to the presence of active micro-organisms, strong fermentation odor, dark color, and catalase enzymes, mild forms of treatment have been developed that eliminate these undesirable properties without significantly degrading the MFC performance. Thus, the MFC fermentation broth may undergo one or more treatments to "polish" the MFC broth, if desired. Polishing primarily improve the aesthetics of the MFC broth rather than changing its performance.

For example, the MFC broth may be treated with one or more mild treatments to provide whitening, deodorizing, and/or concentrating of the MFC without impairing its efficiency. In embodiments, an enzyme treatment may be used to break down cellular and proteolytic material (i.e., debris from the fermentation broth) from the fermentation broth. In other embodiments, the MFC solution may be "polished" or deodorized and/or sterilized by various chemical and physical treatments of the MFC broth. For example, the MFC broth may be deodorized by treatment with oxidizing and/or bleaching agents (e.g., low level concentrations of peroxide compositions such as hydrogen peroxide, sodium perborate, sodium percarbonate, sodium persulfate; sodium hypochlorite, and the like). In one embodiment, the MFC broth may be treated with from about 0.01 to about 1% by weight, from about 0.01 to about 0.50% by weight, or from about 0.01 to about 0.25% by weight of oxidizing and/or bleaching agents without producing measurable losses in performance as compared to the untreated broth. Although higher concentrations of treatment agents also may be possible without affecting performance, but are not typically needed to obtain the desired deodorization and whitening without appreciable residual oxidants remaining. In addition, pasteurization techniques may be used to both sterilize the broth and provide the energy needed to accelerate the reaction of the oxidizing and bleaching ingredients. One of skill in the art can determine appropriate agents, concentrations and reaction conditions which can achieve the desired result without adversely affecting the efficiency of the MFC.

The MFC broth also may be concentrated to increase the solids and remove other undesired fermentation by-products (i.e., organic acids). For example, decanting centrifuges can be used to concentrate the MFC in the broth or concentrate the broth after washing steps between or after treatments without diminishing the MFC concentration in the final broth product due to product losses that are typically experienced with belt presses. In other embodiments, the MFC broth can be diluted to provide a more fluid product or one that can be more easily activated due to its improved flow properties. In the more dilute ranges, a co-agent may be used to improve the homogeneity of the broth or to provide additional dispersion of the MFC fibers in lower surfactant applications like bodywash, shampoo, and liquid handwash. Typical ranges of MFC concentration in the broth range from about 0.5% by weight MFC to over 10% by weight MFC. For example, if concentration methods are used the MFC broth may have up to about 20% by weight MFC.

The mildly treated MFC broth has numerous advantages over other forms of MFC previously available commercially. For example, the mildly treated MFC broth is in a form that it is easier to activate than other forms of MFC, in part due to the elimination of the issues associated with dispersion and hydration of the powder forms of MFC, thereby enabling use of lower shear equipment while providing faster activation times. In addition, the MFC broth can be pre-activated (e.g., passed through high shear mixers such as multi-stage rotor-stator devices or high pressure homogenizers) to yield a solution of fully activated MFC that can be added directly to a wide range of formulations to impart the desired yield value (i.e., suspensional properties) without requiring the use of additional high shear mixing by the end user. For example, to prepare a 3% by weight formulation of AxCel® PX powder MFC (about 60% MFC), activation at 3000 psi requires two passes through a pressure homogenizer, whereas a 2 wt % MFC broth achieves good activation at 1500 psi in one pass through a pressure homogenizer.

The mildly treated MFC broth also has a much wider range of formulation possibilities, especially when co-agents are not included. In addition, the mildly treated broth form of MFC is surprisingly highly efficient with use levels well below the powdered form of MFC. For example, some embodiments of mildly treated MFC broth produced in the Examples had an average increase of 40% in yield value as compared to that of wet-cake forms of MFC, thereby increasing the efficiency of the MFC in many applications, including high surfactant applications.

In embodiments, co-agents can be added to the MFC broth if desired. For example, carboxymethyl cellulose (CMC) is known as an effective co-agent to help prevent flocculation of MFC in high water systems. Also, cationic guar and cationic HEC can be used in the same manner as CMC to prevent flocculation of MFC in high water systems where these polymers are soluble. These cationic polymers can help prevent MFC flocculation in applications such as fabric softeners, hair and skin conditioners, and anti-bacterial hand cleaners and household cleaners that use quaternary amine-based surfactants. Also, there is some evidence that optical brighteners commonly found in laundry detergents can serve as effective co-agents to prevent MFC flocculation, such as CAL Fluor® dyes. Other co-agents that may show more modest benefits to MFC stabilization (by prevention of MFC flocculation) include xanthan gum, diutan gum, welan gum, scleroglucan gum, succinoglucan gum, gellan gum, guar gum, pectin, carrageenan, locust bean gum, gum arabic, hydroxyethyl cellulose, hydroxypropyl cellulose, methylcellulose, carbomer, and non-ionic thickening surfactants such as some Pluronic® surfactants. The co-agents may be present in the MFC broth in as little as 1 part co-agent to 10 parts MFC (e.g., for co-agents such as CMC, cationic guar, and cationic HEC which adsorb onto the fibers and provide a repelling charge) to up to from about 0.25 to about 1% by weight or more for a co-agent that merely provides a viscous matrix to prevent or slow the migration of the fibers together in a formulation.

Thus, embodiments of the present application provide an MFC fermentation broth, or polished versions thereof, in which the MFC is highly efficient. For example, embodiments of the MFC broth may provide an average of greater than about 20%, 30%, 40% or more improvement in yield values as compared to those of previously available commercial forms of MFC. For example, in embodiments the MFC broth may be used such that the concentration of MFC is only about 0.024% and yet provides over 1 Pa of yield value in many surfactant formulations. This increased efficiency of the MFC broth allows for preparation of higher clarity formulations due to the reduced amount of MFC broth required as compared to previously available forms of MFC, since MFC tends to cloud formulations as concentrations rise.

Finally, the compositions and the methods of this disclosure can be useful to provide suspension to non-aqueous systems like PEG solutions used as carrier fluids to suspend hydrocolloids or other particulate material.

The MFC broths provided herein may be useful in a variety of applications. For example, the compositions can be used to make numerous personal care products (e.g., bodywashes, hand soaps, and shampoos) that have both the smooth, rich, thickening properties imparted by surfactant-thickening agents and also the improved suspension properties imparted by the MFC broth. Also, the compositions can be used to make dishwashing soap with suspended actives (e.g., moisturizing beads) or decorative items or laundry detergents with suspended actives, such as insoluble enzymes, encapsulated actives, and zeolites. The compositions and the methods of this disclosure can also be useful with cationic systems like fabric softeners, anti-microbial cleaners, skin lotions, and hair conditioners containing cationic surfactants. In some of the foregoing uses, the addition of a co-agent may provide extra stability to the MFC by preventing flocculation of the MFC fibers that could reduce clarity and possibly destabilize the suspension properties of the formulation.

The MFC broths also can be used in high salt systems, including saturated salt systems, or to thicken or provide suspension in polyol compositions and some alcohol systems. For example, the MFC broth may be used to provide suspension in polyol compositions including PEG 300, glycerine, ethylene glycol, or propylene glycol solutions. Advantageously, this can be done using only the water contributed by the aqueous broth solutions of MFC as it is incorporated.

Advantageously, solutions prepared using the MFC broths are relatively insensitive to their order of addition in high surfactant systems, whereas solutions prepared using powdered MFC have significant sensitivity to order of addition in high surfactant systems and surfactant-thickened systems due to incompatibility with the co-agent in such systems. Use levels of the MFC in these applications can range from about 0.001 to about 0.25% by weight active MFC in the total composition, with more typical use levels from about 0.015 to about 0.06% by weight active MFC in the total composition.

The present disclosure is further illustrated by the following examples, which are not to be construed in any way as imposing limitations upon the scope thereof. On the contrary, it is to be clearly understood that resort may be had to various other embodiments, modifications and equivalents thereof which, after reading the description therein, may suggest themselves to those skilled in the art without departing from the spirit of the present invention and/or the scope of the appended claims.

EXAMPLES

Example 1: MFC Broth Addition to Provide Suspension in Commercial Dish Soap

Step 1: Activate broth MFC solution by using any of several example methods:

i. Lab Scale: 200 g of broth was added to a 200 g closed Oster® puree mixing jar and mixed using an Oster blender at top speed for 5 minutes. This method can typically be used to activate MFC broth solutions with up to 1% active MFC.

ii. Lab Scale: 1000 g of MFC broth was added to a 2 liter plastic beaker and mixed on a Silverson® L4RT-A mixer equipped with the emulsion screen. The broth was mixed for 10 minutes at 10,000 rpm with constant movement of the beaker. This method can typically be used to activate MFC broth solutions with up to 1% active MFC.

iii. Lab Scale to Plant Scale: MFC broth was activated using an APV Gaulin® pressure dual stage homogenizer. Activation can be done up to 1.5% MFC and higher at sufficient pressures and passes. For example, at 0.6-2.0% active MFC broth, activation can be in one pass at as little as 2000 psi.

For the examples listed in the tables below, the Oster puree mixing jar was used.

Step 2: Weigh out the desired amount of Palmolive® Ultra Green Apple Dish Detergent into an 8 oz. jar. A sufficient amount of activated MFC broth was added to the jar containing the dish soap to result in a 0.024% or 0.0336% active MFC.

For the examples listed in the tables below, a 0.6% active MFC diluted broth was used. 8 g of this activated MFC broth solution was used along with 192 g of Palmolive Ultra dish soap (Colgate-Palmolive Company, New York, N.Y.) to provide a 200 g final solution at 0.024% active MFC. Also, 11 g of this activated MFC broth solution was used along with 189 g of Palmolive Ultra dish soap to provide in a 200 g final solution at 0.0336% active MFC. The solution was then mixed for about 5 minutes at 800 rpm using a jiffy mixing blade.

Comparative formulations were prepared using a comparable level of active MFC from an MFC powdered product and an MFC wet-cake lot blend. The wet-cake lot blend was prepare by first making up five 0.5% concentrations of active MFC based on five different lots of MFC wet-cake that were randomly selected. The 0.5% solutions were activated using the Oster blender (puree cup, "liquefy" speed for 5 minutes) and then adding 175 ml of each of the five activated solutions to make a total of 875 ml solution of the 5 lots. This solution was mixed with a jiffy mixing blade at 1000 rpm for 5 minutes.

The formulations were then completely deaerated using a centrifuge at about 150 gs, and the yield was measured using a Brookfield Ultra RV with a #71 vane spindle. The results in Table 1 illustrate the superior performance of a number of unique broth MFCs over a typical powdered MFC in Palmolive Ultra Dish Soap. The results in Table 2 illustrate that this superior efficiency is significant even at higher use levels of MFC.

TABLE 1

Yield Value of Commercial Dish Detergent with MFC Broth vs. Powdered MFC and Wet-Cake MFC

| Batch# | MFC Conc. in Broth/Wet-Cake/Powder | Palmolive Ultra LDD (0.024% MFC) Yield (Pa) | Palmolive Ultra LDD (0.0336% MFC) Yield (Pa) |
|---|---|---|---|
| AxCel ® CG-PX (powdered MFC product) | 60% | 0.40 | 0.79 |
| 5-lot Wet-Cake Blend | 0.50% | 0.95 | 1.53 |
| MFC Broth 1 | 1.300% | 1.18 | 2.49 |
| MFC Broth 2 | 1.324% | 1.24 | 2.50 |
| MFC Broth 3 | 1.140% | 1.34 | 2.49 |
| MFC Broth 4 | 1.160% | 1.24 | 2.40 |
| MFC Broth 5 | 1.040% | 1.24 | 2.54 |
| MFC Broth 6 | 1.220% | 1.18 | 2.24 |
| MFC Broth 7 | 1.377% | 1.13 | 2.60 |
| MFC Broth 8 | 1.200% | 1.72 | 2.49 |
| MFC Broth 9 | 0.701% | 1.59 | 2.92 |
| MFC Broth 10 | 1.237% | 1.32 | 2.34 |

TABLE 2

Yield Value of Commercial Dish Detergent with MFC Broth vs. Powdered MFC and Wet-Cake MFC

| Fermentor Batch# | MFC Conc. in Broth/Wet-Cake/Powder | Palmolive (0.024% MFC) Yield (Pa) | Palmolive (0.0336% MFC) Yield (Pa) | Palmolive (0.0525% MFC) Yield (Pa) | Palmolive (0.075% MFC) Yield (Pa) |
|---|---|---|---|---|---|
| AxCel ® CG-PX (powdered MFC product) | 60% | 0.40 | 0.79 | | 2.23 |
| 5-lot Wet-Cake Blend | 0.50% | 0.95 | 1.53 | 3.13 | 5.54 |
| MFC Broth 1 | 1.300% | 1.18 | 2.49 | 4.26 | 7.34 |
| MFC Broth 2 | 1.324% | 1.24 | 2.50 | 4.61 | 7.79 |
| MFC Broth 3 | 1.140% | 1.34 | 2.49 | 4.53 | 7.66 |
| MFC Broth 4 | 1.160% | 1.24 | 2.40 | 4.50 | 7.45 |
| MFC Broth 5 | 1.040% | 1.24 | 2.54 | 4.44 | 8.36 |
| MFC Broth 6 | 1.220% | 1.18 | 2.24 | 4.34 | 7.35 |
| MFC Broth 7 | 1.377% | 1.13 | 2.60 | 5.57 | 9.38 |
| MFC Broth 8 | 1.200% | 1.72 | 2.49 | 6.15 | 9.84 |

TABLE 2-continued

Yield Value of Commercial Dish Detergent with MFC Broth vs. Powdered MFC and Wet-Cake MFC

| Fermentor Batch# | MFC Conc. in Broth/Wet-Cake/Powder | Palmolive (0.024% MFC) Yield (Pa) | Palmolive (0.0336% MFC) Yield (Pa) | Palmolive (0.0525% MFC) Yield (Pa) | Palmolive (0.075% MFC) Yield (Pa) |
|---|---|---|---|---|---|
| MFC Broth 9 | 0.701% | 1.59 | 2.92 | 4.10 | 9.35 |
| MFC Broth 10 | 1.237% | 1.32 | 2.34 | 4.89 | 8.34 |

Example 2: MFC Broth Addition to Provide Suspension in a Commercial, Liquid Laundry Detergent Compared to Powdered MFC and Wet-Cake MFC Step 1: Activate MFC broth solution using the method detailed in Example 1.

Step 2: Weigh out 189 g of Tide® HE 2× Free and Clear liquid laundry detergent (LLD) (Procter & Gamble, Cincinnati, Ohio) into an 8 oz. jar. A sufficient amount of activated MFC broth was added to the jar containing the dish soap to result in a 0.024% active MFC.

For the examples listed in the table below, a 0.6% active MFC diluted broth was used. 11 g of this activated MFC broth solution was used with 189 g of Tide HE 2× Free and Clear LLD to provide a 200 g final solution at 0.0336% active MFC. The solution was then mixed for about 5 minutes at 800 rpm using a jiffy mixing blade. Comparative formulations were prepared using the method detailed in Example 1. The resulting solutions were then completely deaerated using a centrifuge at about 150 gs, and the yield was measured using a Brookfield Ultra RV with a #71 vane spindle.

TABLE 3

Yield Value of Commercial Laundry Detergent with MFC Broth vs. Powdered MFC

| Fermentor Batch # | MFC Conc in Broth/Wet-Cake/Powder | Tide HE (0.024% MFC) | Tide HE (0.0336% MFC) Yield (Pa) | Tide HE (0.0525% MFC) |
|---|---|---|---|---|
| AxCel® CG-PX (powdered MFC product) | 60% | 0.07 | 0.25 | 0.46 |

TABLE 3-continued

Yield Value of Commercial Laundry Detergent with MFC Broth vs. Powdered MFC

| Fermentor Batch # | MFC Conc in Broth/Wet-Cake/Powder | Tide HE (0.024% MFC) | Tide HE (0.0336% MFC) Yield (Pa) | Tide HE (0.0525% MFC) |
|---|---|---|---|---|
| 5-lot Wet-Cake Blend | 0.50% | 0.59 | | 1.93 |
| 5-lot MFC Broth Blend | 0.50% | 1.06 | | 3.99 |
| MFC Broth 1 | 1.300% | | 1.22 | |
| MFC Broth 2 | 1.324% | | 1.13 | |
| MFC Broth 3 | 1.140% | | 1.28 | |
| MFC Broth 4 | 1.160% | | 1.23 | |
| MFC Broth 5 | 1.040% | | 1.18 | |
| MFC Broth 6 | 1.220% | | 1.33 | |
| MFC Broth 7 | 1.377% | | 1.02 | |
| MFC Broth 8 | 1.200% | | 1.28 | |
| MFC Broth 9 | 0.701% | | 1.59 | |
| MFC Broth 10 | 1.237% | | 1.55 | |

MFC provided as a broth was surprisingly found to have higher efficiency than the wet-cake form of MFC. Although the reason for this is not fully understood, it may be due to some of the limitations of wet-cake recovery and dewatering by belt press which can result in the loss of some fractions of the highest surface area fibers of the MFC. Testing of 5 lots of MFC wet-cake gave an average of 0.97 Pa yield value as measured in a Tide HE 2× liquid laundry detergent at 0.0336% active MFC, whereas the results of 20 broth batches gave an average of 1.36 Pa yield value. A table of results is given below:

TABLE 4

Yield Value of Commercial Laundry Detergent with MFC Broth vs. Wet Cake MFC

| Fermentation Batch# | MFC Conc. | Tide HE 2x (0.0336% MFC) Yield (Pa) | Wet-Cake Form of MFC | MFC Conc. | Tide HE 2x (0.0336% MFC) Yield (Pa) |
|---|---|---|---|---|---|
| MFC broth 1 | 1.300% | 1.22 | wet-cake 1 | 26.5% | 1.30 |
| MFC broth 2 | 1.324% | 1.13 | wet-cake 2 | 19.2% | 0.66 |
| MFC broth 3 | 1.140% | 1.28 | wet-cake 3 | 21.2% | 0.78 |
| MFC broth 4 | 1.160% | 1.23 | wet-cake 4 | 21.2% | 0.88 |
| MFC broth 5 | 1.040% | 1.18 | wet-cake 5 | 21.1% | 1.25 |
| MFC broth 6 | 1.220% | 1.33 | | | |
| MFC broth 7 | 1.377% | 1.02 | | | |
| MFC broth 8 | 1.200% | 1.28 | | | |
| MFC broth 9 | 0.701% | 1.59 | | | |
| MFC broth 10 | 1.237% | 1.55 | | | |
| MFC broth 11 | 1.256% | 1.29 | | | |
| MFC broth 12 | 1.247% | 1.42 | | | |
| MFC broth 13 | 1.336% | 1.83 | | | |
| MFC broth 14 | 1.217% | 1.40 | | | |
| MFC broth 15 | 1.183% | 1.40 | | | |

TABLE 4-continued

Yield Value of Commercial Laundry Detergent with MFC Broth vs. Wet Cake MFC

| Fermentation Batch# | MFC Conc. | Tide HE 2x (0.0336% MFC) Yield (Pa) | Wet-Cake Form of MFC | MFC Conc. | Tide HE 2x (0.0336% MFC) Yield (Pa) |
|---|---|---|---|---|---|
| MFC broth 16 | 1.000% | 1.23 | | | |
| MFC broth 17 | 1.406% | 1.39 | | | |
| MFC broth 18 | 1.14% | 1.55 | | | |
| MFC conc. broth 19 | 2.00% | 1.60 | | | |
| | Average Broth Yield Value: | 1.36 | | Average Wet-Cake Yield Value: | 0.97 |
| | | | 5-lot Wet-Cake MFC Blend | 0.5% | 1.06 |

TABLE 5

Summary of Tables 1-4.

| | Broth Avg. Yield (Pa) | Wet cake Avg. Yield (Pa) | Powder Yield (Pa) |
|---|---|---|---|
| Dish soap: | | | |
| 0.024% MFC | 1.20 | 0.95 | 0.40 |
| 0.0336% MFC | 2.50 | 1.53 | 0.79 |
| 0.0525% MFC | 4.74 | 3.13 | N/A |
| 0.075% MFC | 8.29 | 5.54 | 2.23 |
| Laundry Detergent: | | | |
| 0.024% MFC | 1.06 | 0.59 | 0.07 |
| 0.0336% MFC | 1.36 | 0.97-1.06 | 0.25 |
| 0.0525% MFC | 3.99 | 1.93 | 0.46 |

Example 3: MFC Broth Addition to Provide Suspension in a Various Surfactants and Polyols as Compared to Powdered MFC and Wet-Cake MFC Step 1: Activate MFC broth solution using the method detailed in Example 1, except a 5 lot blend of randomly selected broth was prepared by preparing five 0.5% MFC activated solutions (Oster, puree jar, "liquefy" speed, 5 minutes) and combining 175 g of each to make a total of 875 g of 0.5% MFC broth blend. The mixture was mixed with a jiffy blade for 5 minutes at 1000 rpm.

Step 2: Weigh out 180 g of surfactant or polyol into a 200 ml Oster puree jar. 20 g of activated MFC broth blend or wet-cake MFC blend was added to the jar to result in a 0.05% active MFC concentration. The solution was then mixed for about 5 minutes at top speed on the Oster blender for 5 minutes ("liquefy" speed setting). Comparative formulations were prepared using the method detailed in Example 1. The resulting solutions were then completely deaerated using a centrifuge at about 150 gs, and the yields were measured using a Brookfield Ultra RV or LV with a #71 vane spindle.

TABLE 6

Yield Value of Various Surfactants and Polyols with MFC Broth vs. Wet Cake MFC

| Base Fluid (prior to dilution of MFC solution) | 5-lot MFC Broth Yield (Pa) | 5-lot Wet-Cake MFC Yield (Pa) |
|---|---|---|
| 50% Benzalkonium Chloride | 2.97 | 2.14 |
| 30% Sodium Laureth Sulfate (STEOL CS-230) | 6.24 | 4.09 |
| 30% Cocamidopropyl betain (AMPHOSOL CA) | 0.48 | 0.18 |
| 44% LAS Surfactant (BIO-SOFT D-62-LT) | 7.53 | 6.12 |
| Propylene Glycol | 1.75 | 1.26 |
| PEG 400 | 3.76 | 2.85 |
| 11.6 lb/gal CaCl$_2$ Brine in water | 0.78 | 0.65 |

What is claimed is:

1. A composition comprising:
a) a microfibrous cellulose broth that comprises a fermentation media comprising microbially produced microfibrous cellulose, wherein the microfibrous cellulose broth has not been pasteurized and has not undergone a high alkali treatment, wherein the microbially produced microfibrous cellulose is produced by *acetobacter xylinum*, and
b) a surfactant,
wherein the microfibrous cellulose broth and the surfactant are each present in the composition in an effective amount to produce the composition having a concentration of microfibrous cellulose, such that the composition, after high shear mixing the microfibrous cellulose broth or the composition, has a yield value higher than that of a comparative composition comprising the surfactant and a powdered microfibrous cellulose, a wet cake microfibrous cellulose, or a combination thereof at an amount that imparts to the comparative composition a concentration of microfibrous cellulose which is the same as the mirofibrous cellulose concentration of the composition, after high shear mixing, and
wherein the yield value of the composition and the yield value of the comparative composition are measured on the same equipment using the same methods.

2. The composition of claim 1, wherein the effective amount of microfibrous cellulose broth is such that the microfibrous cellulose concentration is from about 0.001% to about 0.25% by weight of the composition.

3. The composition of claim 1, wherein the effective amount of microfibrous cellulose broth is such that the microfibrous cellulose concentration is from about 0.02% to about 0.075% by weight of the composition.

4. The composition of claim 1, wherein the effective amount of microfibrous cellulose broth is such that the mirofibrous cellulose concentration is from about 0.03% to about 0.075% by weight of the composition.

5. The composition of claim 1, wherein the effective amount of microfibrous cellulose broth is such that the microfibrous cellulose concentration is from about 0.05% to about 0.075% by weight of the composition.

6. The composition of claim 1, wherein the yield value of the composition is at least 20% higher than that of the comparative composition.

7. The composition of claim 1, wherein the yield value of the composition is at least 40% higher than that of the comparative composition.

8. A composition consisting essentially of:
a) a microfibrous cellulose broth consisting of a fermentation media having microbially produced microfibrous cellulose, wherein the microfibrous cellulose broth has not been pasteurized and has not undergone a high alkali treatment, wherein the microbially produced microfibrous cellulose is produced by *acetobacter xylinum*, and
b) a surfactant,
wherein the microfibrous cellulose broth and the surfactant are each present in the composition in an effective amount to produce the composition having a concentration of microfibrous cellulose, such that the composition, after high shear mixing the microfibrous cellulose broth or the composition, has a yield value higher than that of a comparative composition comprising the surfactant and a powdered microfibrous cellulose, a wet cake microfibrous cellulose, or a combination thereof at an amount that imparts to the comparative composition a concentration of mirofibrous cellulose which is the same as the microfibrous cellulose concentration of the composition after high shear mixing, and
wherein the yield value of the composition and the yield value of the comparative composition are measured on the same equipment using the same methods.

9. The composition of claim 8, wherein the effective amount of microfibrous cellulose broth is such that the microfibrous cellulose concentration is from about 0.02% to about 0.075% by weight of the composition.

10. The composition of claim 8, wherein the yield value of the composition is at least 20% higher than that of the comparative composition.

11. A method for improving a yield value of a surfactant composition, comprising:
adding a microfibrous cellulose broth to a composition comprising a surfactant that comprises a fermentation media comprising microbially produced microfibrous cellulose, wherein the microfibrous cellulose broth has not been pasteurized and has not undergone a high alkali treatment, wherein the microbially produced microfibrous cellulose is produced by *acetobacter xylinum*,
wherein the microfibrous cellulose broth and the surfactant are each present in the composition in an effective amount to produce the composition having a concentration of microfibrous cellulose, such that the composition, after high shear mixing the microfibrous cellulose broth or the composition, has a yield value higher than that of a comparative composition comprising the surfactant and a powdered microfibrous cellulose, a wet cake microfibrous cellulose, or a combination thereof at an amount that imparts to the comparative composition a concentration of microfibrous cellulose which is the same as the microfibrous cellulose concentration of the composition after high shear mixing, and
wherein the yield value of the composition and the yield value of the comparative composition are measured on the same equipment using the same methods.

12. The method of claim 11, wherein the effective amount of microfibrous cellulose broth is such that the microfibrous cellulose concentration is from about 0.001% to about 0.25% by weight of the composition.

13. The method of claim 11, wherein the effective amount of microfibrous cellulose broth is such that the microfibrous cellulose concentration is from about 0.02% to about 0.075% by weight of the composition.

14. The method of claim 11, wherein the effective amount of microfibrous cellulose broth is such that the microfibrous cellulose concentration is from about 0.03% to about 0.075% by weight of the composition.

15. The method of claim 11, wherein the effective amount of microfibrous cellulose broth is such that the microfibrous cellulose concentration is from about 0.05% to about 0.075% by weight of the composition.

16. The method of claim 11, wherein the yield value of the composition is at least 20% higher than that of the comparative composition.

17. The method of claim 11, wherein the yield value of the composition is at least 40% higher than that of the comparative composition.

18. The method of claim 11, wherein the composition is a personal care product selected from the group consisting of bodywashes, hand soaps, shampoos, conditioners, and skin lotions.

19. The method of claim 11, wherein the composition is a cleaning product selected from the group consisting of dishwashing soaps, laundry detergents, fabric softeners, and antimicrobial cleaners.

20. The composition of claim 1, wherein the microfibrous cellulose broth is deodorized, sterilized, or a combination thereof.

21. The composition of claim 1, wherein the microfibrous cellulose is present in the microfibrous cellulose broth in a concentration from about 0.25% to about 20% by weight of the microfibrous cellulose broth.

22. The composition of claim 8, wherein the microfibrous cellulose broth is deodorized, sterilized, or a combination thereof.

23. The composition of claim 8, wherein the microfibrous cellulose is present in the microfibrous cellulose broth in a concentration from about 0.25% to about 20% by weight of the microfibrous cellulose broth.

24. The composition of claim 1, wherein the composition has a yield value of at least about 0.48 Pa.

25. The composition of claim 1, wherein the composition has a yield value of at least 1.0 Pa.

26. The composition of claim 1, wherein the microbially produced microfibrous cellulose is present in the microfibrous cellulose broth in an amount of from about 0.5 g/L to about 2 g/L.

27. The composition of claim 8, wherein the microbially produced microfibrous cellulose is present in the microfibrous cellulose broth in an amount of from about 0.5 g/L to about 2 g/L.

* * * * *

UNITED STATES PATENT AND TRADEMARK OFFICE
CERTIFICATE OF CORRECTION

PATENT NO. : 10,292,927 B2
APPLICATION NO. : 13/862031
DATED : May 21, 2019
INVENTOR(S) : J. Swazey et al.

Page 1 of 1

It is certified that error appears in the above-identified patent and that said Letters Patent is hereby corrected as shown below:

In the Specification

Column 4, Line 44, change "improve" to --improves--
Column 5, Line 30, delete "it"
Column 8, Line 12, change "prepare" to --prepared--
Column 11, Line 35, delete "a"

In the Claims

Column 13, Line 33, Claim 8, Line 20, change "mirofibrous" to --microfibrous--
Column 14, Line 52, Claim 24, Line 2, delete "about"

Signed and Sealed this
Twenty-first Day of April, 2020

Andrei Iancu
*Director of the United States Patent and Trademark Office*